United States Patent [19]

Smith et al.

[11] Patent Number: 5,139,485
[45] Date of Patent: Aug. 18, 1992

[54] VERRESS NEEDLE WITH ENHANCED ACOUSTICAL MEANS

[75] Inventors: Kevin W. Smith, Miami; Charles R. Slater, Fort Lauderdale; Frank A. Scarfone, Boca Raton; Gregory J. Murphy, Sunrise; Thomas O. Bales, Jr., Coral Gables; Michael D. Bacon, Hialeah, all of Fla.

[73] Assignee: Ethicon, Inc., Somerville, N.J.

[21] Appl. No.: 695,367

[22] Filed: May 3, 1991

[51] Int. Cl.$^5$ ........................................... A61M 5/178
[52] U.S. Cl. .................................... 604/158; 604/26; 604/274
[58] Field of Search ............ 604/156, 157, 158, 164, 604/26, 159, 170, 117, 274; 128/748

[56] References Cited

U.S. PATENT DOCUMENTS

| | | | |
|---|---|---|---|
| 1,527,291 | 2/1925 | Zorraquin | 604/158 |
| 4,627,841 | 12/1986 | Dorr | 604/158 |
| 4,808,168 | 2/1989 | Warring | 604/158 |
| 4,869,717 | 9/1989 | Adair | 604/26 |
| 4,944,728 | 7/1990 | Carrell et al. | 604/164 |

Primary Examiner—Gene Mancene
Assistant Examiner—Michael Lynch
Attorney, Agent, or Firm—Paul A. Coletti

[57] ABSTRACT

A Verress-type needle which has a sharpened outer needle and allows passage of a blunt inner needle within the outer needle. The Verress needle also contains a position indicator to indicate the position of the inner needle within the outer needle, so that the user knows whether the inner needle is in a protective or non-protective position. Further, a liquid level indicator demonstrates the path of liquid flow within the Verress-type needle. Finally, there is an acoustical enhancement mechanism, which allows the user to know whether the blunt inner needle has sprung forward within the abdominal cavity, to its most forward, protective position.

18 Claims, 2 Drawing Sheets

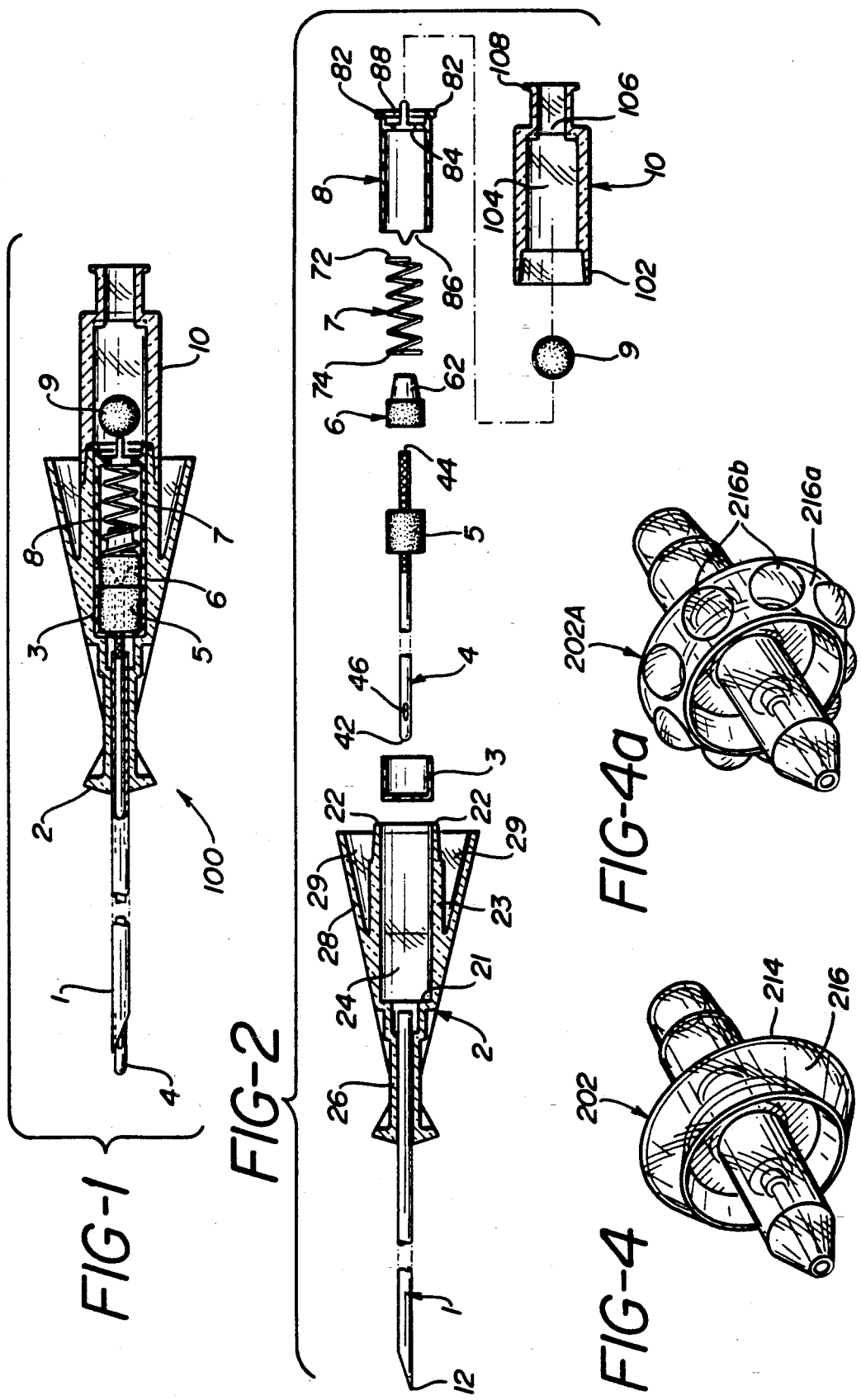

VERRESS NEEDLE WITH ENHANCED ACOUSTICAL MEANS

FIELD OF THE INVENTION

This invention relates to surgical instruments. More particularly, it relates to Verress-type needles. Most specifically, it relates to a Verress-type needle containing a sound amplifying means and liquid level indicating means, which enhance the performance of this needle.

BACKGROUND OF THE INVENTION

Needles to create pneumoperitoneum are used to insufflate the abdominal cavity to facilitate endoscopic examination and surgery. A Verress-type pneumoneedle has a spring-loaded, blunt tipped inner needle contained within a larger diameter piercing needle. The larger diameter needle is hollow and allows for passage of the blunt needle therein. Once the Verress-type needle penetrates the abdominal wall, and enters the body cavity, the resistance against the end of the Verress-type needle is removed, so that the spring force causes the blunt needle to move forward, to extend beyond the sharp tip of the outer needle. This allows the needle to enter the body without puncture or laceration of any abdominal structures.

Verress-type needles use a hollow, blunt inner needle capable of fluid passage, and to carry insufflating gas into the abdominal cavity. A stopcock and valve assembly is connected to the inner needle. The inner needle and valve assemblies are pushed rearward by resistance on the needle end and are biased forward by a spring when the resistance is removed. With this type of design, the needle is grasped like a dart, or in some instances, along outer flanges, like a surgical trocar. In creating these designs, however, it has been found that there are certain perceived drawbacks to these needles.

First, it is difficult to know when the needle is fully inserted into the body. Consequently, there is no visual or audible means to know that: (a) the hollow sharpened outer needle has pierced the peritoneum; (b) the blunt inner needle is no longer rectracted due to a resistant force; or (c) the blunt inner needle has been pushed forward by a preloaded spring, so that it again protects the instrument from damaging any internal organs.

The lack of these functions may cause uncertainty during use of current Verress-type needles.

SUMMARY OF THE INVENTION

Accordingly, it is an object of the invention to provide a needle wherein there are provided audible feedback means in order to determine whether the blunt tip of the inner needle has been expressed forward past the sharpened end of the hollow needle.

It is yet another object of the invention to provide visual means to determine that the blunt tip of the needle has moved forward, past the hollow sharpened outer needle.

It is still another object of the invention to provided a Verress-type needle wherein there is visual means provided to indicate liquid, and into the inflated abdominal cavity. These means may also, desirably, indicate opposite flow, such as leakage of pneumoperitoneum flow within the hollow chamber of the Verress-type needle.

These and other objects of the invention are accomplished in a Verress-type pneumoneedle which contains a hollow outer needle with a sharpened point, allowing passage of a spring-loaded blunt tipped inner needle. This hollow outer needle is placed on a circular handle. Contained within the handle is a sound generator and amplifier, which indicates that the blunt tipped inner needle has been expressed forward, so that its blunt end extends beyond the sharp tip of the outer needle. This helps prevent puncture and laceration of the abdominal cavity after the Verress needle is inserted therein.

Further, the handle contains a lens-magnified color indicator, to indicate the location of the spring-loaded, blunt tipped needle. This feature comprises, ideally, two colored bands that are magnified by a lens. One of the colored bands indicates that the blunt end of the inner needle is moved forward and extends beyond the sharp tip of the outer needle. The opposite colored band indicates that the blunt end of the inner needle has not yet been moved forward. This visual stimulus helps prevent punctures and lacerations of the abdominal cavity by the sharpened tip of the outer needle.

Finally, the handle contains liquid flow indicator means, which positively ascertain for the user whether solutions added to the body through the rear of the inner needle, have passed into the abdominal cavity. This indication asertains for the user that the sharpened end of the outer needle has successfully penetrated the abdominal wall, and entered into the body cavity. In addition, it is desirable for this flow indicating means to permit the user to observe whether there is, at least, a leak of fluid from the pneumoperitoneum.

These and other objects of the invention will be better understood from the attached drawings in which:

DETAILED DESCRIPTION OF THE DRAWINGS

FIG. 1 is a cross-sectional view of Verress-type needle of this invention;

FIG. 2 is an exploded assembly view of a Verress-type needle of this invention;

FIG. 4 and FIG. 4a are perspective views of a cylindrical lens configuration of this invention.

DETAILED DESCRIPTION OF THE INVENTION

Figure 3:
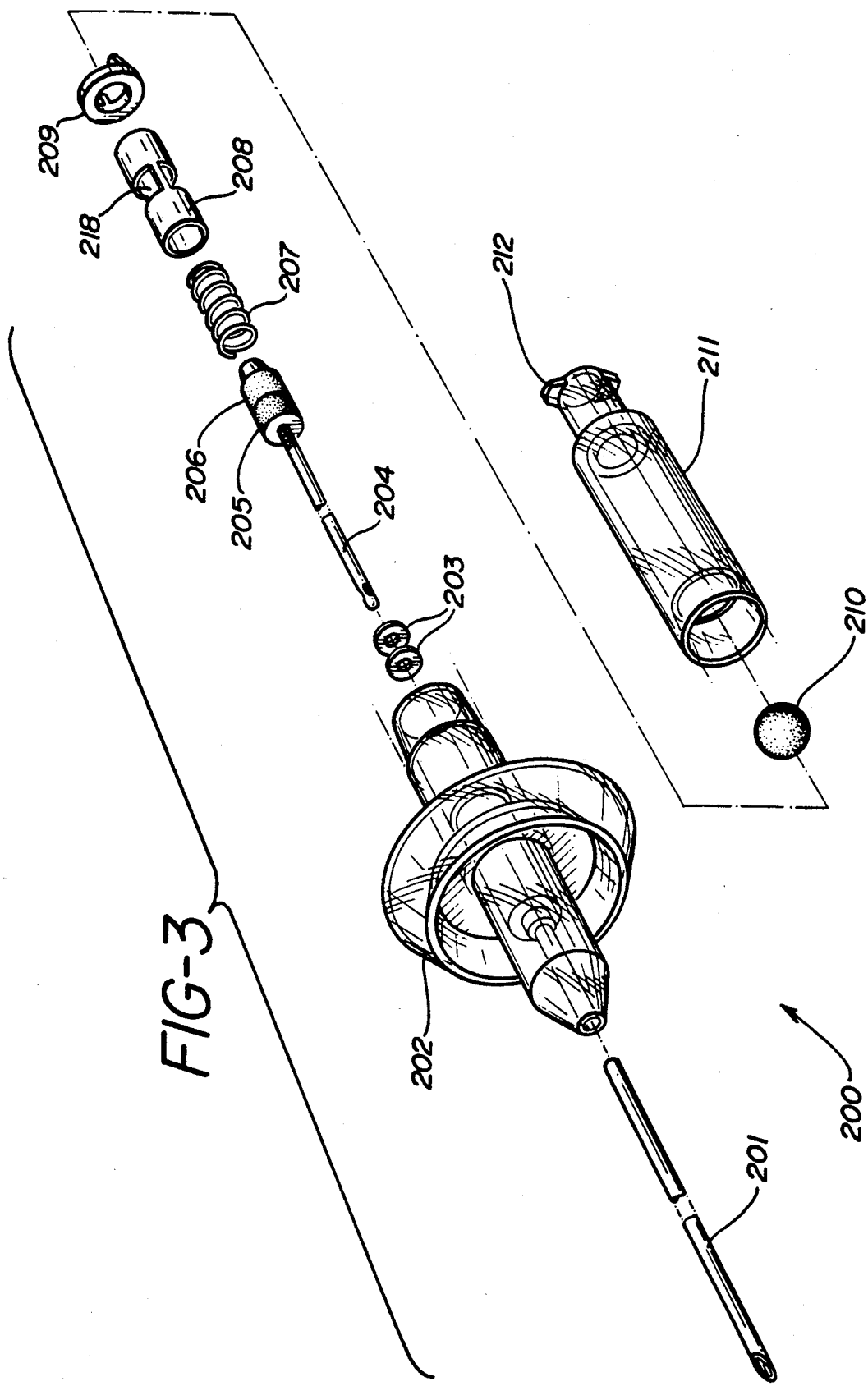
FIG. 3 is a exploded assembly view of an alternate Verress-type needle of this invention.

The Verress-type needle 100, of this invention comprises a hollow outer needle with a sharpened tip 12 maintained in a handle 2. The handle 2 has inserted into it the blunt inner needle 4 with a blunt tip 42, which has a smaller diameter than the hollow outer needle 1. Thus, the blunt inner needle 4 can fit within the outer needle 1 with interior passage therethrough. The inner needle 4 is spring-loaded at the end 72 of a spring 7 against a viewing tube 8. The other end 74 of spring 7 is placed against cone shaped end 62 of positive indicator 6. Positive indicator 6 slides over inner needle 4 to abut negative indicator 5, as will be later explained herein. Viewing tube 8 fits with flanges 82 against walls 22 of handle 2.

Handle 2 has a hollow interior bore 24 extending for a portion of the length of handle 2 containing narrow walls 26, in a generally cylindrical fashion. Outer needle 1 is anchored to handle 2 within the bore 24 at walls 26. Also, inner needle 4 is hollow, for insufflation through end 44 and from sufflation holes 46.

Therefore, when properly assembled, the blunt tip 42 of inner needle 4 is caused by the force of the spring 7 to extend past the tip 12 of the sharpened hollow outer needle 1. When inserted into the body, pressure is exerted first against the blunt tip 42 of the inner needle 4. Needle 4 is caused to retract into the handle 2 of instrument 100, and then the body wall contacts the sharpened tip 12 of the outer needle 1. When the outer needle 1 is inserted into the body, it pierces the body wall. Then, the force of spring 7 is greater than any tissue force, so that spring 7 pushes the blunt inner needle 4, whereby the blunt inner needle 4 is caused to surpass the tip 12 of the sharpened outer needle 1. In this way, the blunt inner needle 4 protects the internal abdominal cavity from damage by the hollow sharpened outer needle 1.

Various aspects of this type of Verress-needle will now be discussed. First, it is to be noticed that the outer walls 28 on handle 2 are cone shaped. There is contained within these walls 28 of the handle 2 a hollowed out portion 29 toward the rear of the handle. This hollowed out portion 29 acts as a sound amplification means. In this way, after the blunt inner needle 4 is caused return to its initial position by the force of the spring 7, the force of the negative indicator 5 (attached to the blunt inner needle 4) against inner wall 21 of the handle bore 24, causes a vibration within handle 2. This vibration is amplified by the hollowed out area 29 at the rear of handle 2. In this way, the user is able to audibly verify the fact that the blunt inner needle 4 has been caused to move into a protective position, so that it is able to protect the abdominal cavity from injury by outer needle 1.

Optionally, and ideally, this sound amplification arrangement is magnified by the opaque washer 3 emplaced within the bore 24 of the handle 2. Thus, when the negative indicator 5 is forced by spring 7 to move against inner wall 21, the washer 3 is also vibrated, and this increased vibration is amplified by the cone shaped hollow portion 29 of handle 2.

Also, there are provided visual means for indication that the blunt inner needle 4 is being forced against the handle 2, such that the tip 42 of blunt inner end 4 extends past the end 12 of the sharpened hollow outer needle 1. This is accomplished by the indicator system 5, 6 attached to the blunt inner needle 4, near the spring 7 which exerts force on the blunt inner needle 4. The spring 7 is located at the rear 84 of the viewing tube 8. This viewing tube 8 is hollow and made of opaque plastic and held within the widened walls 23 of the bore 24 contained in handle 2. The viewing tube 8 has a clear window 86 located toward its distal end, which serves to indicate whether the inner needle 4 is exposed past the length of the outer needle 1.

The visual indication means is a two part indicator 5, 6 which is attached to the inner needle 4. The lower portion 5 of the inner needle is colored in a negative fashion, such as red. The upper portion 6, most closely attached to the spring 7, is colored in a positive manner, such as green. In this way, when the inner needle 4 is in its initial postion, it is fully extended past the sharpened end 12 of the outer needle 1. Only the green positive indicator 6 is exposed in the window 86 of the viewing tube 8. Negative indicator 5 is obscured by opaque washer 3. However, when the needle 4 is retracted, by force applied to the blunt tip 42 of inner needle 4, the lower, negative indicator 5 is exposed so that the observer sees red in the viewing window 86. Positive indicator 6 is obscured by opaque viewing tube 8. In this fashion, the viewer knows that the sharpened outer needle end 12 is exposed, and that there is a likelihood of harm to the patient if the inner needle 4 does not return to its initial position. (Alternately, the viewer can see both red and green at this point, if window 86 is made larger than indicated. This visual stimulus will elicit a similar reaction for the user.)

One additional visual mechanism is contained in the handle 2 at cap 10. Cap 10 is attached to the rear of the handle 2 by sliding walls 102 over walls 22. Cap 10 contains a hollow tube 104 with a colored ball 9 contained therein. This colored ball 9 rises or falls within the tube 104 depending upon liquid level within the tube 104 and, ultimately, inner needle 4. Therefore, the user may insert saline solution through the end 106 of cap 10. It will be caused to flow into inner needle 4, and then into the abdominal cavity. If there has been proper insertion of the needle 100, ball 9, which is less dense than saline solution, will float toward the rear 106 of cap 10, for so long as saline remains to that level in needle 100. Once saline has drained into the abdominal cavity, so that cap 10 empties, ball 9 will begin to flow to the forward end of cap 10, abutting end 88 of tube 8. This procedure will work simarly, if liquid flow is in an opposite direction.

At the end 106 of the cap 10, there is a luer connector 108, which may be connected to a stopcock or valve. With a stopcock in the closed position, the internal abdominal pressure is sealed, so that pneumoperitoneum is maintained.

As is further seen in FIG. 3, there is disclosed a Verress-type needle 200 similar to the embodiment in FIG. 1, except that it contains an acoustical mechanism on its forward part of the handle 202 which is slightly different from that described in FIGS. 1 and 2. This acoustical mechanism can also be seen in FIG. 4. There, the rear of the mechanism is horn-shaped as at 214, so that when the washers 203 vibrate by motion of the inner needle 204 against the handle 202, the sound is further amplified.

Other portions of the needle 200 are identical in function to those of needle 100. That is there are described an outer needle 201, a pair of washers 203, an inner needle 204, indicating means 205, 206, a spring 207, and a viewing window 208, held within handle 202. This viewing window 208 is obscured, except for a narrow opening 218, through which positive viewing means 206 and negative viewing means 205 may be observed. A two piece cap 209, 211 is attached to handle 202, and floating ball 210 is maintained within the cap 209, 211. There is also a luer lock 212 at the end of the cap.

As can be further seen in FIG. 4a, the portion of the acoustical mechanism 214 on FIG. 4 has been enhanced in handle 202a. While the acoustical horn 214 in FIG. 4 is created so that there is maintained a cylindrical lens 216 on the acoustical horn 214, FIG. 4a now contains acoustical mechansim 216a containing magnifying lenses 216b around its periphery . The cylindrical lens 216 and magnifying lenses 216a visually enhance the colored indicators 205, 206 as they pass through the focal point of each of the lenses, so that the user may more clearly see the color change as indicators 205, 206 move with inner needle 204. In this fashion, the user can determine more clearly which the puncture has been made by the sharpened outer needle 201.

This invention has been described with a number of preferred embodiments, all of which accomplish the aforementioned objects of the invention. It is to be understood that the invention is to be derived from the following claims and their equivalents.

We claim:

1. A Verress-needle comprising:

a handle having proximal and distal ends connected to a hollow outer needle with an end portion for penetrating a body cavity, said hollow outer needle and said handle providing a conduit through which fluid may be passed to or from the body cavity, said hollow outer needle attached to said handle at the distal end of said handle;

a hollow inner needle having proximal and distal ends surrounding an elongated body, which extends through said hollow outer needle and into said conduit in said handle, said inner needle having an opening near its distal end, and an open portion at its proximal end within said handle;

a spring housed within said conduit of said handle at said proximal end of said handle and said inner needle for biasing said inner needle forwardly to a protective position, so that the distal end of said inner needle extends past the end portion of said outer needle absent resistance against said inner needle; and acoustical means contained on said handle for amplifying the sound of said inner needle being moved by said spring to its protective position.

2. The needle of claim 1 wherein said acoustical means is a cone shaped horn contained on said handle.

3. The needle of claim 1 wherein said acoustical means is a washer within said handle interacting with said inner needle.

4. The needle of claim 3 wherein said acoustical means further comprises a cone-shaped horn contained on said handle.

5. The needle of claim 4 wherein said needle further comprises a lens contained on said horn.

6. The needle of claim 5 wherein said needle further comprises a plurality of magnifying lenses contained on said horn, said horn having a cylindrical shape and said magnifying lenses contained on the periphery of said cylinder.

7. A Verress-needle comprising:

a handle having proximal and distal ends, and connected to a hollow first needle, said first needle having an end portion for penetrating a body cavity, said first needle providing a conduit to pass fluid relative to said body cavity, said first needle attached to said handle at said handle distal end;

a second needle having proximal and distal ends and an elongated body, said second needle placed in concentric engagement with said first needle and into said conduit in said handle; said second needle having an opening at its distal end and an open portion at its proximal end within said handle;

one of said needles connected to a spring, said spring capable of biasing said needles with respect to each other so that said needles are placed in relative slidable engagement one to the other and said spring causing said second needle to be placed in a protective position covering the end portion of said first needle;

acoustical means contained on said handle for amplifying the sound of said second needle being moved by said spring means into said protective position.

8. The needle of claim 7 wherein said acoustical means is a cone-shaped horn contained on said handle.

9. The needle of claim 7 wherein said acoustical means is a washer within said handle interacting with said second needle.

10. The needle of claim 9 wherein said acoustical means further comprises a cone-shaped horn contained on said handle.

11. The needle of claim 10 wherein said needle further comprises a lens contained on said horn.

12. The needle of claim 11 wherein said needle further comprises a plurality of magnifying lenses contained on said horn, said horn having a cylindrical shape and said magnifying lenses contained on the periphery of said cylinder.

13. A Verress-needle comprising a pair of concentric needles with at least one of said needles having a hollow inner cylinder such that said other needle fits within said hollow inner cylinder, and said needles slidable with respect to one another, each of said needles held within a handle, said handle containing spring means for biasing a first of said needles to a first position with respect to the second of said needles, and said handle further connected to acoustical means for amplifying the sound of said first needle moving into said first position.

14. The needle of claim 13 wherein said acoustical means is a cone-shaped horn contained on said handle.

15. The needle of claim 14 wherein said acoustical means is a washer within said handle interacting with said first needle.

16. The needle of claim 15 wherein said acoustical means further comprises a cone-shaped horn contained on said handle.

17. The needle of claim 16 wherein said needle further comprises a lens contained on said horn.

18. The needle of claim 17 wherein said needle further comprises a plurality of magnifying lenses contained on said horn, said horn having a cylindrical shape and said magnifying lenses contained on the periphery of said cylinder.

* * * * *